United States Patent [19]
Prior et al.

[11] Patent Number: 6,096,309
[45] Date of Patent: Aug. 1, 2000

[54] COMPOSITIONS CONTAINING THROMBIN AND MICROFIBRILLAR NANOMETER COLLAGEN, AND METHODS FOR PREPARATION AND USE THEREOF

[75] Inventors: Jeffrey J. Prior, Redwood City; Donald G. Wallace, Menlo Park; David H. Sierra, Atherton; Frank A. DeLustro, Belmont, all of Calif.

[73] Assignee: Cohesion Technologies, Inc., Palo Alto, Calif.

[21] Appl. No.: 09/099,126

[22] Filed: Jun. 17, 1998

Related U.S. Application Data

[63] Continuation-in-part of application No. 08/878,471, Jun. 18, 1997, abandoned.

[51] Int. Cl.⁷ .................................................. A61K 38/00
[52] U.S. Cl. ......................... 424/94.63; 424/94.1; 514/2; 514/21; 530/356; 530/380; 530/381; 530/382; 435/13; 435/188
[58] Field of Search .......................... 435/13, 188; 514/2, 514/21; 530/356, 380, 381, 382; 424/94.1, 94.63

[56] References Cited

U.S. PATENT DOCUMENTS

| | | |
|---|---|---|
| 2,433,299 | 12/1947 | Seegers . |
| 4,215,200 | 7/1980 | Miyata et al. . |
| 4,359,049 | 11/1982 | Redl et al. . |
| 4,363,319 | 12/1982 | Altshuler . |
| 4,420,339 | 12/1983 | Kato . |
| 4,515,637 | 5/1985 | Cioca . |
| 4,722,948 | 2/1988 | Sanderson . |
| 4,874,368 | 10/1989 | Miller et al. . |
| 4,891,359 | 1/1990 | Saferstein et al. ......................... 514/21 |
| 5,077,049 | 12/1991 | Dunn et al. . |
| 5,110,730 | 5/1992 | Edgington et al. . |
| 5,116,315 | 5/1992 | Capozzi et al. . |
| 5,218,137 | 6/1993 | Porter et al. . |
| 5,219,328 | 6/1993 | Morse et al. . |
| 5,226,877 | 7/1993 | Epstein . |
| 5,290,552 | 3/1994 | Sierra et al. . |
| 5,318,524 | 6/1994 | Morse et al. . |
| 5,405,607 | 4/1995 | Epstein . |
| 5,407,671 | 4/1995 | Heimburger et al. . |
| 5,464,471 | 11/1995 | Whalen et al. . |
| 5,476,777 | 12/1995 | Holly et al. . |
| 5,616,689 | 4/1997 | Shenoy et al. . |
| 5,631,011 | 5/1997 | Wadström . |

FOREIGN PATENT DOCUMENTS

| | | |
|---|---|---|
| 28502/92 | 5/1993 | Australia . |
| 0302754 | 2/1989 | European Pat. Off. . |
| 0 341 007 | 11/1989 | European Pat. Off. . |
| 0478827 | 4/1992 | European Pat. Off. . |
| 0524803 | 1/1993 | European Pat. Off. . |
| 0538951 | 4/1993 | European Pat. Off. . |
| 2041942 | 9/1980 | United Kingdom . |
| WO 86/01814 | 3/1986 | WIPO . |
| WO 90/01959 | 3/1990 | WIPO . |
| WO 91/00046 | 1/1991 | WIPO . |
| WO 92/09301 | 6/1992 | WIPO . |
| WO 94/02172 | 2/1994 | WIPO . |
| WO 94/20133 | 9/1994 | WIPO . |
| WO 96/31245 | 10/1995 | WIPO . |
| WO 96/17633 | 6/1996 | WIPO . |
| WO 97/04081 | 2/1997 | WIPO . |

OTHER PUBLICATIONS

Doillon et al. "Porosity and biological Properties of Poly–ethylene Glycol–Conjugated Collagen Materials". *Journal of Biomaterials Science, Polymer Edition*, vol. 6, No. 8(1994), pp. 715–28.

Teppler et al. "Prolonged Immunostimulatory Effect of Low–Dose Polyethylene Glycol Interleukin 2 in Patients with Human Immunodeficiency Virus Type 1 Infection". *Journal of Experimental Medicine*, vol. 177(Feb. 1993), pp. 483–492.

Balleisen et al., "Comparative investigation on the influence of human bovine collagen types I, II and III on the aggregation of human platelets" *Klin. Wschr.* (1975) 53:903–905.

Balleisen et al., "Platelet–collagen interaction. The influence of native and modified collagen (Type 1) on the aggregation of human platelets" *Haemostatis* (1976) 5:155–164.

Capaldi et al., The C–terminal extrahelical peptide of Type 1 collagen and its role in fibrillogenesis in vitro *Biopolymers* (1982) 21:2291–2313.

Carter et al., "Clinical experience with crude preparations of growth factors in healing of chromic wounds in human subjects" *Growth Factors and Other Aspects of Wound Healing/Biological and Clinical Implications* (1988) Alan R. Liss, Inc., pp. 303–317.

Chabbat et al., "Properties of a new fibrin glue stable in liquid state" *Thrombosis Res.* (1944) 76:525–533.

"Chem Sources—U.S.A." Chemical Sources International, Inc. (1994 Edition) Fernandina Beach, Florida 32034–6190.

Colman et al., "Section A. Plasma Coagulation Factors. Overview of hemostasis" *Hemostasis and Thrombosis 3rd Edition* (1994) J. P. Lippincott. Chapter 1, pp. 3–18.

Cornell et al., "Multicenter trial of collagraft as bone graft substitute" *J. Orthopaedic Trauma* (1991) 5:1–8.

Damus et al., "A purified procoagulant enzyme from the venom of the eastern diamondback rattlesnake (*Crotalus adamanteus*): In vivo and in vitro studies" *J. Lab. Clin. Med.* (1972) 79:906–923.

(List continued on next page.)

*Primary Examiner*—Jeffrey Stucker
*Attorney, Agent, or Firm*—Foley & Lardner; Laurie A. Axford

[57] ABSTRACT

The present invention relates to thrombin-containing hemostatic compositions, their preparation and use. In particular, it relates to hemostatic compositions comprising stabilized thrombin and microfibrillar collagen in an aqueous medium. In a preferred embodiment of the present invention, the compositions are used in a kit comprising two different components, one of which is autologous patient's plasma as the source of fibrinogen, and the other of which is the thrombin-containing composition which also contains microfibrillar collagen having an average diameter of about 3–30 nanometers.

66 Claims, 1 Drawing Sheet

OTHER PUBLICATIONS

DePalma et al., "The preparation of fibrinogen concentrate for use as fibrin glue by four different methods" *Transfusion* (1993) 33:717–720.

Doi et al., "Dynamics of rod–like macromolecules in concentrated solution Part 1." Cavendish Laboratory, Cambridge University, Cambridge, England (1977) pp. 560–570.

Doi et al., "Dynamics of rod–like macromolecules in concentrated solution Part 2." Cavendish Laboratory, Cambridge University, Cambridge, England (1977) pp. 918–932.

Ellis et al., "The ideal tissue adhesive in facial plastic and reconstructive surgery" *J. Otolaryngology* (1990) 19:68–72.

Ferry, "The nature of viscoelastic behavior" *Viscoelastic Properties of Polymers, 3rd Edition* (1980) John Wiley, New York. Chapter 1, pp. 1–31; Chapter 2, pp. 41–44.

Gelman et al., "Collagen fibril formation in vitro" *J. Biol. Chem.* (1979) 254:11741–11745.

Gestring et al., "Autologous fibrinogen for tissue–adhesion, hemostasis and embolization" *Vasc. Surg.* (1983) 17:294–304.

Hatsuoka et al., Hemostatic effects of microfibrillar collagen hemostat (MCH) in experimental coagulopathy model and is mechanism of hemostatis *Thrombosis Res.* (1986) 42:407–412.

Janmey et al., "Effects of actin filaments on fibrin clot structure and lysis" *Blood* (1992) 80:928–936.

Jorgensen et al., "Expression of completely γ–carboxylated recombinant human prothrombin" *J. Biol. Chem.* (1987) 262:6729–6734.

Kaufman et al., "Expression, purification, and characterization of recombinant γ–carboxylated factor IX synthesized in Chinese hamster ovary" *J. Biol. Chem.* (1986) 261:9622–9628.

Keefe et al., "Clinical use of injectable bovine collagen: A decade of experience" *Clin. Materials* (1992) 9:155–162.

Le Bonniec et al., "Thrombin Glu–39 restricts the P'3 specificity to nonacidic residues" *J. Biol. Chem.* (1991) 266:13796–13803.

Le Borgne et al., "Amidase activity and thermal stability of human thrombin" *Applied Biochem./Biotechnol.* (1994) 48:125–135.

Lundén, "Additional coagulation factors" *Plasma Proteins* (1979) Blomback, Hansen, eds., John Wiley & Sons, New York, pp. 285–288.

Matras, "Fibrin seal: The state of the art" *Oral Maxillofac. Surg.* (1985) pp. 605–611.

McPherson et al., "Collagen fibrillogenesis in vitro: A characterization of fibril quality as a function of assembly conditions" *Collagen Rel. Res.* (1985) 5:119–135.

Miletich et al., "Purification of human coagulation factors II, IX, and X using sulfated dextran beads" *Meth. Enzymol.* (1981) 80:220–228.

Nesheim et al., "The kinetics and cofactor dependence of the two cleavages involved in prothrombin activation" *J. Biol. Chem.* (1983) 258:5386–5391.

Oshima et al., "Stimulation by dextran sulfate of denaturation of bovine thrombin" *Thrombosis Res.* (1987) 47:59–67.

Piez, "Collagen" *Encyclopedia of Polymer Science and Engineering* (1985) 3:699–727.

Raccuia et al., "Comparative efficacy of topical hemostatic agents in a rat kidney model" *Am. J. Surgery* (1992) 163:234–238.

Rapaport et al., "The tissue factor pathway: How it has become a 'prima ballerina'" *Thrombosis and Haemostasis* (1995) 74:7–17.

Rezaie, "Tryptophan 60–D in the B–insertion loop of thrombin modulates the thrombin–antithrombin reaction" *Biochem.* (1996) 35:1918–1924.

Rosenblatt et al., "Dynamic rheological studies of hydrophobic interactions in injectable collagen biomaterials" *J. Appl. Polymer Science* (1993) 50:953–963.

Rosenblatt et al., "The effect of collagen fiber size distribution on the release date of proteins from collagen matrices by diffusion" *J. Controlled Release* (1989) 9:195–203.

Rotoli et al., "Optimizing and stabilizing thrombin activity" *Haematologica* (1986) 71:463–466.

Saltz et al., "Experimental and clinical applications of fibrin glue" *Plastic and Reconstructive Surgery* (1991) pp. 1005–1015.

Segel, "Behavior and analysis of rapid equilibrium and steady–state enzyme systems" *Enzyme Kinetics* (1975) John Wiley & Sons, New York, pp. 931–942.

Siedentop et al., "Autologous fibrin tissue adhesive" *Laryngoscope* (1985) 95:1074–1076.

Sierra, "Fibrin sealant adhesive systems: A review of their chemistry, material properties and clinical applications" *J. Biomaterials Appl.* (1993) 7:309–352.

Tidrick et al., "Fibrin fixation of skin transplants" *Surgery* (1944) 15:90–95.

Wallace et al., "Multiple denaturational transitions in fibrillar collagen" *Biopolymers* (1986) 25:1875–1893.

Wallace et al., "Shear creep of injectable collagen biomaterials" *J. Biomedical Materials Res.* (1987) 21:861–880.

Wood et al., "Expression of active human factor VIII from recombinant DNA clones" *Nature* (1984) 312:330–336.

Wu et al., "Single amino acid substitutions dissociate fibrinogen–clotting and thrombomodulin–binding activities of human thrombin" *Proc. Natl. Acad. Sci. USA* (1991) 88:6775–6779.

Ye et al., "Glycosaminoglycan contributions to both protein C activation and thrombin inhibition involve a common arginine–rich size in thrombin that includes residues arginine 93, 97, and 101" *J. Biol. Chem.* (1994) 269:17965–17970.

Young et al., "Fibrin suture of peripheral nerves. Measurement of the rate of regeneration" *The Lancet* (1940) pp. 126–128.

COMPOSITIONS CONTAINING THROMBIN AND MICROFIBRILLAR NANOMETER COLLAGEN, AND METHODS FOR PREPARATION AND USE THEREOF

RELATED APPLICATIONS

This application is a continuation-in-part of U.S. patent application Ser. No. 08/878,471 filed Jun. 18, 1997, now abandoned, the specification of which is incorporated herein in its entirety.

TECHNICAL FIELD

The present invention relates to compositions for use in the field of tissue treatment and repair. More particularly, the subject matter of the present invention relates to hemostatic compositions comprising thrombin and microfibrillar collagen.

BACKGROUND ART

The physiological pathway which is involved in hemostasis and tissue repair is initiated by the release of thromboplastin from injured cells. Upon contact with factor VII in the surrounding plasma, factor X activator is formed. Together with factor V, along with associated phospholipids and calcium, prothrombin is converted into thrombin. The enzymatic activity of thrombin results in cleavage of fibrinogen to form fibrin monomers, which aggregate and are covalently crosslinked via the activity of factor XIIIa (which is formed via thrombin activation of factor XIII). See FIG. 1.

In order to promote rapid hemostasis and wound healing, many clinicians have focused on the development of hemostatic compositions which include various coagulation factors and function by exploiting the body's own hemostatic processes. For example, fibrin powder has been used as a hemostatic agent for many years. In the mid 1900s, surgeons began to use fibrin-containing preparations as in situ fibrin polymerizing agents. To initiate fibrin clot formation in such compositions, concentrated plasma and ground tissue (muscle or lung) were often used as the as the catalyst for peripheral nerve anastomosis (Young, et al., *Lancet* 2:126–8, 1940.) In 1944, Tidrick et al. utilized human plasma and bovine thrombin in solution as a two-part sealant to attach skin grafts (Tidrick, et al., *Surgery* 15:90–95 (1944)). The use of plasma and thrombin for these and other applications soon fell out of favor due to premature failure of the bond. This was attributed to low mechanical strength, which was in turn attributed to low fibrinogen concentration.

Fibrin sealants utilizing concentrated fibrinogen in the form of homologous cryoprecipitate were reported by Matras, et al. in *Oral Maxillofac. Surg.* 43:605–611 (1985). These types of fibrin sealants are commercially available under the name Tisseel® (Immuno AG, Vienna, Austria) and Beriplast P® (Centeon AG, Germany), and are reviewed in Sierra, *J Biomater. Appl.*, 7:309–352 (1993). However, these types of fibrin sealants generally involve the administration of pooled blood products.

In an effort to avoid the problems associated with administration of pooled blood products, some investigators turned to the use of tissue sealant compositions utilizing patient autologous plasma as a source of fibrinogen, which was then applied in combination with bovine topical thrombin in calcium chloride solution (see, e.g., Siedentop, et al., *Laryngoscope* 95: 1074–1076 (1985)). However, performance of these materials was somewhat limited because of their inferiority in comparison to the ready-to-use homologous products. In addition, the use of these materials is limited due to performance and method of use problems associated with the variability of properties of the autologous plasma.

These problems have led to the development of hemostatic compositions which are based on the use of polymeric materials as adhesives. For example, synthetic polymerizable compositions such as cyanoacrylates have been used in adhesive compositions (Ellis, et al., *J. Otolaryngol.* 19:68–72 (1990)). However, the toxicity of many of these synthetic polymer compositions has limited their usefulness.

Natural substances can also exhibit bonding characteristics. In particular, collagen has been reported as being useful as a hemostatic agent (U.S. Pat. No. 4,215,203.) However, when compared with either collagen or synthetic polymers, adhesives which depend on fibrin exhibit enhanced hemostasis (Raccula, et al., *Am. J Surg.* 163 (2): 234–238 (1992)).

Thrombin-based formulations for use as hemostatics have also previously been described. See, for example, U.S. Pat. Nos. 2,433,299 and 4,363,319. However, the use of thrombin in hemostatic formulations is limited by its instability during storage. Accordingly, many investigators have turned to the use of thrombin in dry form, or its use in conjunction with a substrate such as a solid matrix. In particular, U.S. Pat. No. 4,515,637 describes the use of thrombin and collagen in the formation of sponges for use in treating wounds. Additionally, U.S. Pat. No. 5,464,471 describes the formation of dry thrombin formulations which are used in conjunction with fibrin monomers.

Recent developments have also led to the production of thrombin-fibrin compositions, which are formulated and used either as "dual component" compositions, or "single component" compositions. In either case, such compositions are sometimes referred to as "fibrin glue", with the thrombin functioning as the "catalyst" component of the glue, and the fibrin functioning as the "resin" component of the glue. Dual-component compositions generally involve the use of separate fibrinogen-containing and thrombin-containing components which are mixed together shortly before or simultaneously upon administration. See, for example, U.S. Pat. No. 5,290,552, which describes a dual-component composition that may optionally contain collagen in the fibrinogen-containing component. Single-component compositions generally include both a source of thrombin and a source of fibrin.

In either the single-or dual-component compositions, the fibrin is usually supplied in the form of fibrinogen, which is then converted to fibrin by thrombin. Although the single-component systems are more convenient to use, these compositions generally require the thrombin to be maintained in an inactive state prior to use to prevent premature coagulation. This problem has been addressed in the following two U.S. Patents: U.S. Pat. No. 5,318,524 describes the development of single-component hemostatic compositions containing thrombin which has either been inactivated or physically separated (using different phases) from fibrinogen prior to use; and U.S. Pat. No. 5,407,671 describes a single-component composition containing a thrombin inhibitor along with the thrombin.

The present invention relates to thrombin-based hemostatic compositions which can reproducibly and effectively be used as a single-component, or in conjunction with a source of fibrinogen, such as autologous plasma. By employing microfibrillar collagen as an additional component in the compositions, many of the aforementioned shortcomings of other hemostatic agents can be avoided.

DISCLOSURE OF THE INVENTION

In accordance with the present invention, it has been discovered that particularly efficacious hemostatic compositions can be formulated by combining thrombin together with microfibrillar collagen. The microfibrillar collagen acts to improve the functionality of the compositions, and also plays an important role in the kinetics of fibrin clot formation, as well as the overall physical characteristics of the fibrin clot.

The thrombin can be derived from a variety of natural sources, such as from pooled animal plasma. For example, bovine thrombin is readily available from a wide variety of commercial sources. In addition, recombinant thrombin can be utilized, which can be synthesized from a variety of recombinant sources such as transformed host (bacterial, yeast or mammalian) cells. In addition, thrombin-like compounds such as certain proteolytic snake venoms, as well as thrombin precursors such as prothrombin can also be used as the source of thrombin for use in the present invention.

The microfibrillar collagen which is useful in the present invention preferably has an average fibril diameter of about 3 to 30 nm. As such, its melting temperature as determined using differential scanning calorimetry is between about 42 to 46° C.

In one embodiment of the present invention, the hemostatic composition further comprises calcium ions, which are added to increase the effective calcium ion concentration at the site of application to an amount which will provide for adequate clot formation. When used at sites having sufficient endogenous calcium ions present, it is not necessary for calcium ions to be added. However, calcium ions are effective at promoting microfibril formation from fibrillar collagen. Accordingly, if the compositions of the present invention are formed from fibrillar collagen, it is desired to add sufficient calcium ions to the composition to form microfibrillar collagen.

The hemostatic compositions of the present invention contain thrombin which remains sufficiently active to be useful for the intended application. Stability depends on various factors, such as temperature and the presence/absence of added means for stabilizing or destabilizing thrombin. However, it is preferable that the thrombin retains 80% or more of its activity at 2–8° C. for at least 6 months.

In a preferred embodiment of the compositions of the present invention, PEG is included to stabilize thrombin. The PEG can be of any suitable molecular weight, such as about 1,000 to 8,000. Additionally, the PEG can be present in a wide range of concentrations, such as 0.1 to 2%, but is preferably present at a concentration of 0.1 to 0.3%.

Since it is desirable to maintain the stability of thrombin upon storage of the hemostatic compositions of the present invention, a further aspect of the present invention involves employing means for stabilizing the thrombin, which can include decreasing the pH to below 6.6, adding a sugar, adding PEG, adding a reversible thrombin inhibitor, adding a calcium chelator and adding a protein.

Another aspect of the present invention is a kit which comprises a thrombin plus microfibrillar collagen containing composition and a source of fibrinogen. The fibrinogen can be added directly to the thrombin-containing composition, or it can be supplied as a separate component in an aqueous medium. A preferred aqueous medium comprising fibrinogen is plasma, and more preferably, it is human plasma, and most preferably it is autologous plasma. In another aspect of the kits of the present invention, a suspension of platelets can be used in conjunction with the thrombin-containing composition, since platelets are activated by thrombin, which initiates the clotting cascade and can effect fibrin clot formation in the absence of exogenously supplied fibrinogen.

In yet another aspect of the present invention, a method for promoting hemostasis of a tissue site on or in the body of a mammalian subject is provided, which entails providing a thrombin-containing composition which additionally contains microfibrillar collagen as one component, and providing a separate fibrinogen solution in an aqueous medium as another component, mixing these two components immediately before contact with the tissue site, then contacting the mixture with the tissue site. In a preferred embodiment of this method, the fibrinogen is supplied in the form of plasma, and more preferably autologous plasma which involves the further step of separating the plasma from the subject's blood.

The method additionally involves the use of a delivery device which is designed for administering multi-component compositions to a treatment site. Such delivery devices can provide for mixing of the two components immediately prior to their being delivered out of the device, or they can alternatively provide for mixing of the two components after exiting the device, such as when sprayed from the device, but before contacting the tissue site.

In still another aspect of the present invention, a method for making hemostatic agents is provided, which comprises the steps of combining together, in no particular order, thrombin, fibrillar collagen and a fiber disassembly agent which is present in sufficient quantities to cause the fibrils to disassemble into microfibrils, and incubating the mixture for an adequate length of time and temperature for the microfibrils to form and become stable. In a preferred embodiment of this method, the fibril disassembly agent is calcium ions, which are preferably present at a concentration of between 10 and 200 mM.

Another embodiment of the present invention relates to compositions comprising collagen that is in the form of a mixture of microfibrillar and non-microfibrillar fibrillar collagen. What is intended by the term non-microfibrillar fibrillar collagen is collagen having fibrils that are larger than microfibrils. In particular, compositions comprising mixtures of microfibrillar collagen and non-microfibrillar fibrillar collagen in a ratio of at least 1:1 (w/w), respectively, may be useful for certain applications. For example, mixtures of microfibrillar collagen and fibrillar collagen with larger fibril sizes may be more flowable and thus easier to use in spraying apparatuses.

Other aspects of the present invention are provided throughout the pecification, and although not specifically mentioned in this section, they are considered part of the present invention.

BEST MODE FOR CARRYING OUT THE INVENTION

Figure 1:
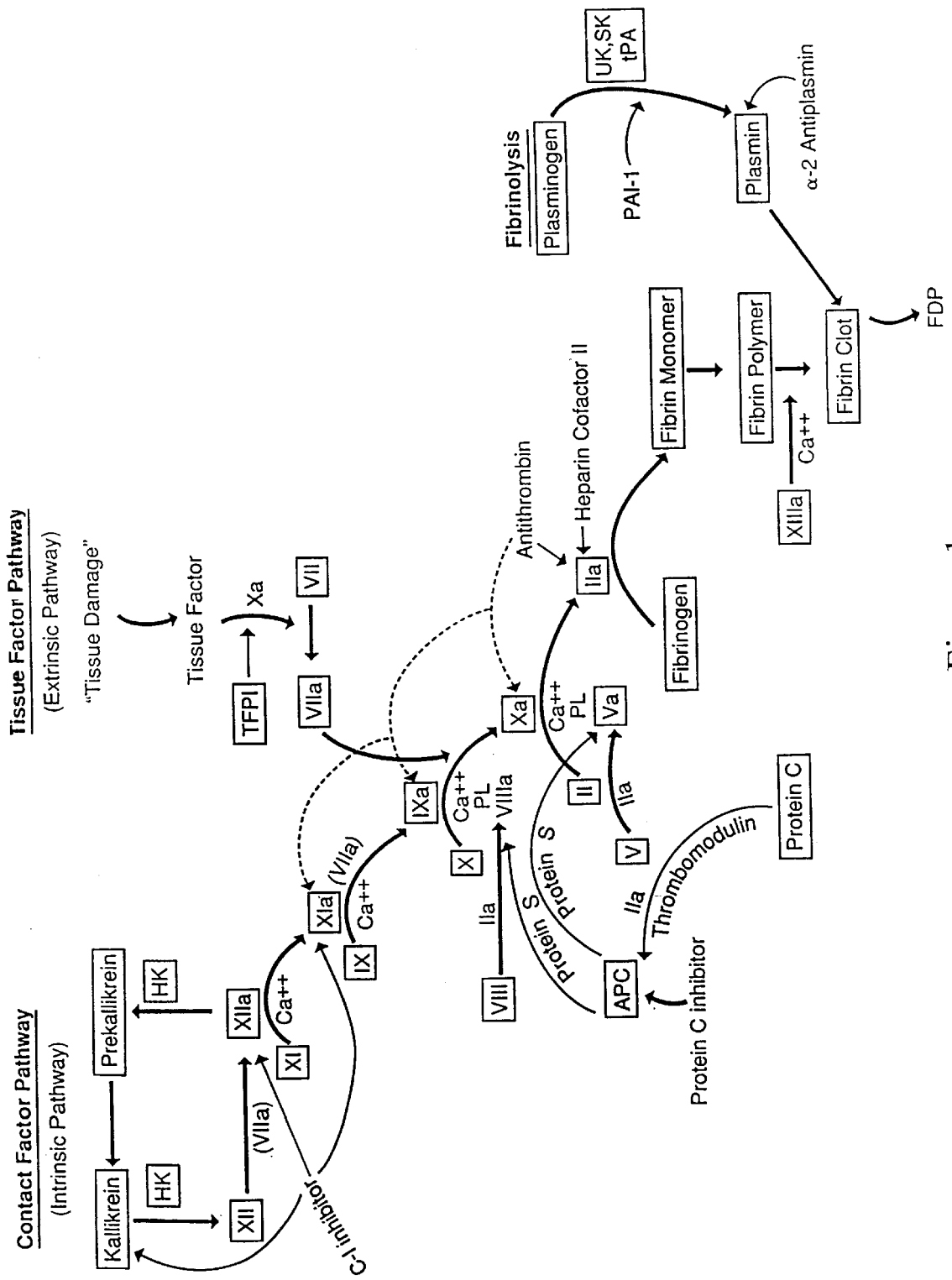
FIG. 1 is a flow chart showing the blood coagulation cascade. (From Enzyme Research Laboratories, Inc., South Bend, Ind.) The abbreviations for the various blood coagulation factors are included in TABLE I.

The present invention relates to the use of thrombin-based compositions to promote hemostasis. More particularly, the thrombin-based compositions comprise thrombin and microfibrillar collagen.

Blood coagulation is a complex cascade of events that results in formation of fibrin strands. FIG. 1 illustrates the blood coagulation cascade. The various factors, their molecular weights and typical plasma concentrations are given in TABLE I.

TABLE I

Plasma Concentrations of Blood Coagulation Factors

| Component | Molecular Weight (daltons) | Plasma Concentration (μg/ml) | Plasma Concentration (μM) |
| --- | --- | --- | --- |
| Fibrinogen (I) | 330,000 | 3000 | 9.09 |
| Prothrombin (II) | 72,000 | 100 | 1.388 |
| Factor V | 330,000 | 10 | 0.03 |
| Factor VII | 50,000 | 0.5 | 0.01 |
| Factor VIII | 330,000 | 0.1 | 0.0003 |
| Factor IX | 56,000 | 5 | 0.08928 |
| Factor X | 58,800 | 8 | 0.13605 |
| Factor XI | 160,000 | 5 | 0.031 |
| Factor XII | 80,000 | 30 | 0.375 |
| Factor XIII | 320,000 | 10 | 0.03124 |
| Protein C | 62,000 | 4 | 0.0645 |
| Protein S | 69,000 | 10(free) | 0.1449 |
| Protein Z | 62,000 | 2.2 | 0.0355 |
| Prekallikrein | 86,000 | 50 | 0.5814 |
| HK | 110,000 | 70 | 0.6363 |
| Fibronectin | 450,000 | 300 | 0.6667 |
| Antithrombin III | 58,000 | 290 | 5 |
| Plasminogen | 90,000 | 216 | 2.4 |
| Urokinase | 53,000 | 0.1 | 0.001887 |
| Heparin Cofactor II | 66,000 | 90 | 1.3636 |
| Alpha$_2$-Antiplasmin | 63,000 | 60 | 0.9524 |
| Protein C Inhibitor | 57,000 | 4 | 0.0702 |
| Alpha$_2$-Macroglobulin | 725,000 | 2100 | 2.8966 |

Thrombin

The primary role of thrombin in the coagulation pathway is its ability to catalyze the conversion of fibrinogen (which may already present at the site of application and/or may be exogenously supplied) to fibrin monomers. Thrombin also plays other important roles in coagulation. For example, thrombin also functions to induce coagulation by activating platelets, which triggers the coagulation cascade. In addition, thrombin catalyzes the conversion of factor XIII to its active form, factor XIIIa, which in turn brings about the covalent crosslinking of the fibrin clot.

Once formed, fibrin monomers aggregate together to form a fibrin clot. The clot can then be further stabilized by covalent crosslinking via factor XIIIa. The microfibrillar collagen which is included in the compositions and thus present during this process of clot formation becomes an integral part of the fibrin clot and thereby alters its properties in a beneficial fashion.

The amount of thrombin which is necessary in the compositions of the present invention is an amount which is sufficient to catalyze the formation of a stable fibrin clot. A clot is considered stable once the formulation is converted from a soft, paste-like liquid to a rubbery gel. This change can be quantified using rheological measurements as described below under Examples. Preferably, the thrombin is present in the hemostatic composition at a concentration of about 10 to 2,000 National Institute of Health (NIH) units/ml, and more preferably from about 300 to 1,000 NIH units/ml.

Thrombin activity, i.e. its efficiency in forming fibrin from fibrinogen, can be determined using a commercially available fibrometer, and comparing the rate of fibrin clot formation using test preparations to those having known thrombin activity. However, thrombin is still suitable for use in the hemostatic compositions of the present invention, even if it does not function well in this test, provided it is still capable of activating platelets. This is because platelet activation catalyzes the formation of a stable clot at an actively bleeding application site via the normal functioning of the coagulation cascade, which is not dependent on exogenously supplied thrombin for fibrinogen cleavage.

Thrombin can be derived from a variety of natural sources. In particular, bovine thrombin is commercially available in lyophilized form (Parke-Davis, Morris Plains, N.J.; GenTrac, Inc., a subsidiary of Jones Medical Industries, Inc., Middleton, Wis.). Thrombin can also be purified from a source of prothrombin complex as described by Chabbat, et al., *Thrombosis Research*, 76(6):525–533 (1994). In addition, thrombin can also be derived from recombinant sources. For example, Jorgensen, et al. have described an expression system for gamma-carboxylated recombinant prothrombin (*J. Biol. Chem.* 262:6729–6734 (1987)).

Truncated and mutated forms of prothrombin can also be prepared and utilized in the present invention. Le Bonniec, et al. describe cloning of pre-thrombin-2 cDNA (pre-thrombin-2 is a pro-thrombin minus residues 1–155 out of 579 total residues) and cloning and expression of a single amino acid replacement mutant (*J. Biol. Chem.* 266:13796–13803 (1991)). Other references which describe mutated or truncated prothrombins are: Ye, et al., *J. Biol. Chem.* 269:17965–17970 (1994); Rezaie, et al., *Biochemistry* 35:1918–1924 (1996); U.S. Pat. No. 5,476,777 (1995); and Wu, et al., *PNAS* 88:6775–6779 (1991). When the recombinant product is prothrombin, conversion to thrombin can be achieved using a complex of coagulation factor Va, factor Xa, and synthetic phospholipids, or with certain snake venom proteases.

Although not preferred, it is possible to use thrombin precursors (e.g. prothrombin) in the hemostatic compositions of the present invention, along with means for conversion to thrombin if such means are not already present at the application site. In addition, thrombin-like compounds such as snake venom proteases which are also capable of forming fibrin clots from fibrinogen are also contemplated by the present invention. (See, e.g. Damus, et al., *J. Lab. Clin. Med.* 79:906–923 (1972)). Accordingly, the term "thrombin" as used herein includes thrombin precursors and thrombin-like compounds, and refers to any protein or amino acid polymer derived from natural or synthetic sources which is capable of catalyzing the formation of fibrin clots from fibrinogen and/or activating platelets.

Collagen

The presence of collagen in the hemostatic compositions of the present invention serves to enhance both the mechanical and physiological properties of these compositions. For example, the collagen serves to increase the viscosity of the compositions, which makes them easier to apply to a site without exhibiting run-off. This acts to control the thrombin concentration at the site of application. Additionally, collagen plays a structural role in clot formation by serving to reinforce the clot. Collagen also serves as an activator of blood platelets which can further promote hemostasis.

Collagen has long been recognized as a component of biomaterials for medical and surgical use. See, e.g., Keefe, et al., *Clinical Materials* 9:155–162 (1992). Collagen can exist in non-fibrillar or fibrillar form. Non-fibrillar collagen consists of triple helices which are approximately 300 nm long and 1.5 nm in diameter (Piez, *Encyclopedia of Polymer Science and Engineering*, Vol. 3, 2nd Ed., John Wiley 699–727 (1985)). In comparison, fibrillar collagen may exist in a wide array of fibrillar sizes. The smallest fibrils arise when 5 to about 30 triple-helical molecules associate. Such associated fibrils have diameters between about 3 to about 30 nm and are roughly 400–500 nm in length. These are generally referred to as "micro-fibrils," (Gelman, et al., *J. Biol. Chem.* 254:11741–11745 (1979).) Larger fibrils, ranging from 30 to 1000 nm in diameter, and being about 1000 to 5000 nm in length, can also be prepared (Capaldi, et al., *Biopolymers* 21:2291–2313 (1982)).

Collagen fibril size can easily be determined using differential scanning calorimetry (DSC) to measure melting temperatures. In general, non-fibrillar collagen melts at 39–40° C., whereas microfibrillar collagen melts at 42–46° C. See, for example, Wallace, et al., *Biopolymers* 25:1875–1893 (1986).

Collagen fibrils are not readily soluble in aqueous medium and instead form particulate suspensions when added to an aqueous medium. However, as used herein, the term "collagen solution" is not intended to exclude such suspensions of fibrillar collagen. The term "fibrillar collagen" as used herein is meant to refer to collagen in fibrillar form, either micro-fibrils or large fibrils. Additionally, a collagen suspension that consists mostly of micro-fibrils (80% or greater) is referred to herein as a "microfibrillar" collagen suspension.

The viscosity of collagen solutions is influenced by collagen fiber size. For example, solutions of non-fibrillar collagen are more viscous than suspensions of fibrillar collagen (Wallace, et al., *J. Biomed. Mater. Res.* 21: 861–880 (1987).) Additionally, suspensions of smaller fibrils of collagen (i.e., microfibrillar collagen) are more viscous than suspensions of larger fibrils of collagen. As described therein, there are two reasons why microfibrillar collagen suspensions are more viscous than suspensions of collagen with larger fibrils. First, the viscosity of fibrillar collagen suspensions is proportional to the number density of the fibrils. Since microfibrils are smaller, at the same percentage of total solids, the number density of a microfibrillar collagen suspensions is greater than that of a suspension of collagen having larger fibrils.

Second, the viscosity of rod-like suspensions is dependent on the length-to-width ratio, such that rods with greater length-to-width ratios tend to be more viscous. Doi, et al.,*J. Chem. Soc. Faraday II,* 74:560–570 and 918–932 (1978). Micro-fibrils are known to be more elongated than larger fibrils. For example, it has been reported that micro-fibrils have a length-to-width ratio of roughly 20 to 130, whereas intermediate-sized fibrils have a length-to-width ratio of roughly 6 to 75. See, e.g., Table II of Wallace, et al., *Biopolymers* 25:1875–1893, (1986). Hence, microfibrillar collagen suspensions are more viscous than collagen suspensions consisting of larger fibrils.

Even though solutions of non-fibrillar collagen are also viscous, fibrillar collagen is still preferred because of its role in enhancing platelet activity. As described by Balleisen, et al., collagen must at least be in multimeric form (either as fibrils or a precipitate) to promote platelet aggregation (*Hemostasis* 5:155–164 (1976)). Also described therein is that non-fibrillar methylated collagen precipitates in the presence of plasma proteins and thereafter serves as an effective enhancer of platelet aggregation. Hence, although microfibrillar collagen is preferred in the practice of the present, methylated collagen is also a suitable form of collagen if administered to a site at which its interaction with intrinsic plasma proteins causes it to precipitate. Platelet aggregation can be measured using a commercially available aggregation meter. The aggregation of platelets causes an increase in light transmission, which can be recorded and expressed as the time required to reach one-half the maximum transmission.

Microfibrillar collagen is easily prepared using known methods, and can be used directly to form the hemostatic compositions of the present invention. Alternatively, fibrillar collagen can be used, such that upon further processing and storage of the compositions, the fibrils will become disrupted. In general, there are many types of compounds which are known in the art which disrupt fibril formation, which may also act to convert fibrillar forms to microfibrillar forms. For example, the presence of salts can function to disrupt collagen fibrils. Specifically, Zyderm® (greater than 70% by volume fibrils of greater than 30 nm in diameter, Collagen Corporation, Palo Alto, Calif.), which is 3.5% by weight fibrillar collagen in 130 mM sodium chloride can be added to the aqueous medium of the hemostatic compositions. When Zyderm® is present at a concentration of 20 mg/ml along with 75 mM sodium chloride, the addition of more salt (20 to 40 mM calcium chloride) can function to disrupt the collagen fibrils upon storage at 5–8° C. for 3–5 hours. This results in conversion of the collagen to a microfibrillar form. Alternatively, 200–500 mM sodium chloride alone can be used to form microfibrillar collagen. See Examples, and in particular TABLE III.

Other disassembly agents which can be included for the purpose of converting fibrillar to microfibrillar collagen include, but are not limited to, glycerol, sucrose and related polyols, such as maltose, sorbitol and mannitol.

It is also possible to use non-fibrillar collagen as the starting material by including a compound such as PEG at an approximate concentration of 3–8%, which acts to form microfibrillar collagen from nonfibrillar collagen. Other compounds which can form microfibrillar collagen from non-fibrillar collagen are also well known in the art.

As discussed throughout the specification, and in particular in the Examples below, the concentration and size of collagen fibrils in an aqueous medium is influenced by the storage conditions, such as the pH, temperature, the presence and concentration of other components in the medium, etc. Such conditions can easily be controlled and adapted to optimize the desired collagen fibril characteristics using the teachings of the present specification in combination with well known principles of collagen chemistry. For example, a mixture of microfibrillar collagen and non-microfibrillar fibrillar collagen may result from storage of microfibrillar ccollagen at room temprature in the presence of compounds known to cause collagen fibril formation. However, as long as the conditions are properly controled, such aggregation may not necessarily proceed to the point at which the collagen is less than half microfibrillar (which would not be desirable), and may even be desired to make the composition more flowable, since larger fibrils tend to be less viscous.

Calcium Ions

A source of calcium ions is necessary to promote clot formation. As described above, calcium ions can also promote disassembly of fibrils, which can be used to form microfibrils from a fibrillar collagen. Calcium ions are usually added to the hemostatic composition in the form of calcium chloride. Alternatively, a sufficient level of calcium may already be present at the application site, in which case addition of calcium ions is not necessary. The amount of calcium ions necessary is an amount which is effective to promote clot formation upon administration. Additionally, if the hemostatic composition is formulated from fibrillar collagen, thus necessitating disassembly of collagen fibrils before application, the amount of calcium ions present will also be that which is necessary to convert the fibrillar collagen to the microfibrillar form.

It is important to note that, at certain relative concentrations, the presence of sodium chloride can interfere with fibril disassembly via calcium ions. For example, at 40 mM calcium chloride and 30 mM sodium chloride, microfibrillar formation is inhibited. This may be due to the opposite charge on the calcium and chloride ion, which may lead to ion-ion charge complexes, which in turn lower the activity of either ion relative to collagen. If calcium chloride is present alone, or if calcium chloride and sodium chloride are present at higher concentrations (e.g., 100 mM calcium chloride and 30 to 130 mM sodium chloride or 40 mM calcium chloride and 150 mM sodium chloride), fibril disassembly is not inhibited.

In determining the amount of calcium ions to include in the hemostatic compositions of the present invention, it is also necessary to consider the presence of other constituents in the fibrinogen source or at the site of application. For example, if the hemostatic composition is formulated for use as a two-component composition (as more fully described below) with plasma as the second of the two components, it should first be determined whether the plasma will be derived from a source already containing calcium ions, or from a source which is depleted of calcium. In particular, citrated plasma is a convenient source of plasma, and citrate is an effective calcium chelator which will prevent the availability of calcium for participation in clot formation. If this is the case, then the desired total effective (nonchelated) calcium concentration should be determined, and the appropriate amount of calcium should be added to achieve this total effective concentration.

Thrombin Stabilizers

In a preferred embodiment of the present invention, the thrombin is stable (i.e. it remains active) during storage in an aqueous medium. In particular, the thrombin is preferably stable for at least 30 days at 18–22° C., and more preferably for at least 60 days at 18–22° C. It is well known that stability of pharmaceutical compositions at a lower temperature can be estimated by evaluating their stability at higher temperatures. See, e.g., Segel, et al., *Enzyme Kinetics*, John Wiley & Sons, New York, pages 932–941 (1975.) In the particular case of thrombin-containing compositions, it has been determined that the stability at 18–22° C. is roughly one tenth to one twelfth of the expected stability at 2–8° C. >See, e.g., European Patent Application 478,827 A1. Accordingly, the hemostatic compositions of the present invention, having been demonstrated to be stable for at least one month at 18–22° C. are expected to be stable for at least 10 months at 2–8° C., and are preferably stable for at least 6 months at 2–8° C. It has also been determined that compositions comprising aqueous suspensions of mixtures of microfibrillar and nonmicrofibrillar fibrillar collagen are stable for at least 12 months at 2–8° C.

Thrombin is known to exhibit autocatalysis brought about by thrombin-thrombin interactions. Accordingly, in order to ensure that the thrombin remains functional, the aqueous medium is preferably maintained at a low pH, in which case thrombin activity is inhibited. For example, the thrombin-containing component of the present invention is maintained at a pH preferably below about 6.6, and more preferably below about 5.7, and is formulated in a manner that will allow the pH to increase upon delivery or at the application site. Other substances which can be added to the aqueous medium to help stabilize thrombin are as follows:

TABLE II

Thrombin Stabilizers

| Stabilizers Added | Reference |
| --- | --- |
| Bovine serum albumin | Rotoli, et al., Haemotologia |
| PEG, 8000 MW | 71: 463–466 (1986) |
| Gelatin | Topfer, et al., EPO 478 827 A1 |
| Polybrene | (1990) |
| (1,5 dimethyl-1.5 di-aza-undecamethylene poly methobromide) | |
| PEG, 6000 MW | Oshima, et al., Thrombosis Res. |
| Bovine serum albumin | 47: 59–67 (1987) |
| Glycerol | LeBorgne, et al., Applied |
| Ethylene glycol | Biochem. Biotechnol. |
| PEG, 6000 MW | 48: 125–135 (1994) |

The inclusion of hydrophilic polymers such as polyalkyl oxides, preferably polyethylene glycol (PEG), in the thrombin-based hemostatic compositions serves to stabilize the thrombin by inhibiting thrombin-thrombin interactions, which prevents autocatalysis. PEG can be added to the hemostatic formulation in admixture, or it can be premixed with thrombin. However, the addition of excess PEG favors formation of fibrillar collagen and should be avoided. The amount of PEG to be added is easily determined by adjusting the concentration to optimize stabilization and fiber size. Generally, PEG is present below 2%, and is preferably below 1%, and more preferably approximately 0.1 to 0.3%.

Additional stabilizers include sugars (e.g. sorbitol, mannitol, glucose, sucrose) and amino acids (e.g. glycine) as described in EPO 478,827A1; EPO 302,754B1; and GB2, 041,942A. Still other means for stabilizing thrombin are described in U.S. Pat. Nos. 5,219,328; 5,318,524; and 5,407,671.

Biologically Active Agents

In addition to their role in hemostasis, the compositions of the present invention may serve as effective delivery vehicles for a wide variety of components that have various desirable physical, chemical, biological and/or therapeutic effects at the site of application or on the body of the subject. For example, antibiotics can be supplied to the application site to prevent infection. Such antibiotics are well known, as are their dosage amounts and means of incorporation. Additionally, antifibrinolytic agents such as aprotinin, C1-esterase inhibitor and ∈-amino-n-caproic acid can be included to enhance clot integrity.

It is also possible to include one or more growth factors in the hemostatic composition to promote wound healing at the site of application, such as platelet-derived growth factors, insulin-binding growth factors, fibroblast growth factors, transforming growth factors, platelet factors and heparin binding growth factors. See, for example, *Growth Factors and Other Aspects of Wound Healing: Biological and Clinical Implications*, Alan R. Liss, Inc., New York, N.Y., pp. 303–329 (1988).

The incorporation of biologically active agents such as drugs into tissue sealant compositions has already been extensively described. See, for example, PCT WO 96/17633. Virtually any biologically active agent which can be incorporated into such a tissue sealant can also be incorporated into the hemostatic compositions of the present invention.

Formulation

The hemostatic compositions of the present invention are formulated for administration in an aqueous medium which may optionally contain buffers, viscosifiers, osmolality enhancers and other substances that are desired and/or necessary to assure biocompatibility, injectibility and efficacy. Depending on the particular application, the compositions can be formulated in various different configurations. For example, a single-component composition containing thrombin and microfibrillar collagen in an appropriate aqueous medium can be utilized for effecting hemostasis at an application site that already has a source of fibrinogen, along with the other clotting factors and conditions which are necessary for the conversion of fibrinogen to fibrin. In other instances, for example if the site of application is not an actively bleeding site, it may be necessary to supply a source of fibrinogen (and any other clotting factors which may be deficient at the treatment site), either in the same single-component composition or as a separate component. However, when thrombin and fibrinogen are included in the same single-component composition, it is necessary to maintain thrombin in an inactive state such that it will be activated upon application.

In two-component compositions, one of the components will necessarily contain thrombin and microfibrillar collagen, and the second component will contain a source of fibrinogen. Although not preferred for lack of convenience, it may also be desired to supply calcium in a separate third component, since calcium ions are necessary for various hemostatic functions, including activation and function of factor XIII, platelet functions, such as aggregation, and finally, for further production of active clotting factors in blood. Accordingly, the absence of calcium may help maintain thrombin stability. In either case, it is preferable for the collagen to be supplied separately from the fibrinogen component, so that during application adequate mixing can be achieved between the thrombin and the fibrinogen.

The fibrinogen source can be synthetic or natural. For convenience, plasma can be used as the fibrinogen source. Preferably, the plasma is human, and more preferably autologous plasma, which is an effective way of avoiding the transfer of infectious agents and other undesirable constituents sometimes found in pooled plasma. The autologous plasma is generally harvested from citrated (0.32–0.38% w/v) blood, which is preferably drawn within a few hours before use. Platelet-rich plasma is separated from the blood using known methods, for example, by centrifugation at 90×G for 10 min., or at 1000×G for 3 min.

Given below are various alternative multi-component embodiments which may be combined together for use in various volume:volume ratios of A:B, such as 0.4:1.0, 1.0:1.0, 1.0:0.4, and 1.0:2.0, with 1:1 being preferred.

| Two-Component Composition (1): | |
|---|---|
| Component A: | Type I fibrillar collagen (20 mg/ml)<br>Calcium chloride (40 mM)<br>Thrombin (at least 500 NIH units/ml)<br>Sodium chloride (150 mM)<br>PEG (0.2% w/v, 1000 MW)<br>Mannitol (15 mM)<br>pH 4.7–6.6 |
| Component B: | Platelet-rich plasma in 0.32–0.38% sodium citrate |

| Two-Component Composition (2): | |
|---|---|
| Component A: | Type I fibrillar collagen (20 mg/ml)<br>Calcium chloride (20 mM)<br>Thrombin (at least 500 NIH units/ml)<br>Sodium chloride (300 mM)<br>PEG (0.2% w/v, 1000 MW)<br>Mannitol (15 mM)<br>pH 4.7–6.6 |
| Component B: | Human fibrinogen 5 mg/ml<br>in 20 mM sodium chloride<br>10 mM sodium phosphate, pH 7.5<br>15 mM mannitol |

| Two-Component Composition (3): | |
|---|---|
| Component A: | Type I fibrillar collagen (20 mg/ml)<br>Calcium chloride (20 mM)<br>Thrombin (at least 500 NIH units/ml)<br>Sodium chloride (300 mM)<br>PEG (0.2% w/v, 1000 MW)<br>Mannitol (15 mM)<br>pH 4.7–6.6 |
| Component B: | Plasma depleted of fibrinogen by heat, or serum, plus blood platelets at 2–4 × $10^8$/ml |

| Two-Component Composition (4): | |
|---|---|
| Component A: | Type I fibrillar collagen (20 mg/ml)<br>Calcium chloride (20 mM)<br>Thrombin (at least 500 NIH units/ml)<br>Sodium chloride (300 mM)<br>PEG (0.2% w/v, 1000 MW)<br>Mannitol (15 mM)<br>pH 4.7–6.6 |
| Component B: | Blood platelets at 2–4 × $10^8$/ml in isotonic saline plus suitable stabilizer excipients for platelets. |

In an alternative embodiment, the following three-component composition can be used, with each of the three components, A:B:C, being mixed in a volume ratio of approximately 0.4–2.0:0.4–2.0:0.4–2.0, with 1:1:1 being preferred.

| Three-Component Composition: | |
|---|---|
| Component A: | Type I fibrillar collagen (30 mg/ml)<br>Calcium chloride (40 mM)<br>PEG (0.2% w/v, 1000 MW) |
| Component B: | Thrombin (at least 1000 NIH units/ml)<br>Sodium chloride (370 mM)<br>Mannitol (15 mM)<br>pH 4.7–6.6 |
| Component C: | Platelet-rich plasma in 0.32–0.38% sodium citrate |

In a more preferred three component composition, the PEG is included with Component B containing the thrombin to facilitate stabilization of the thrombin as follows:

| Three-Component Composition (2): | |
|---|---|
| Component A: | Type I fibrillar collagen (30 mg/ml)<br>Calcium chloride (40 mM) |
| Component B: | Thrombin (at least 1000 NIH units/ml)<br>Sodium chloride (370 mM)<br>PEG (0.2% w/v, 1000 MW)<br>Mannitol (15 mM)<br>pH 4.7–6.6 |
| Component C: | Platelet-rich plasma in 0.32–0.38% sodium citrate |

Testing of Clot Formation

The hemostatic compositions of the present invention interact with fibrinogen to form a gelatinous clot at the site of application. This clot acts as a physical barrier to blood flow. Thus, the efficiency of these compositions is proportional to the strength of the clots they can form. In addition, the thrombin in the composition clots any blood which is present at the site, which adds to the efficiency of the composition to promote hemostasis.

The clotting efficiency of the hemostatic compositions can easily be determined by observing instantaneous clot formation upon administration. However, in order to compare the efficiency of clot formation of various different formulations for purposes of optimization, such comparisons can be made on the basis of rheometric measurements which are taken during clot formation. As described by Rosenblatt, et al. (*J. Appl. Polym. Sci.* 50: 953–963 (1993)), the dynamic elastic modulus, G', and the dynamic viscous modulus, G", are determined as a function of the elasticity and the overall strength of a gel, respectively. (See, also, Ferry, *Viseoelastic Properties of Polymers*, 3d ed., John Wiley, New York, pages 1–31 and 41–44 (1980); and Janmey, et al., *Blood*, 80(4): 928–936 (1992)).

Use and Administration

The compositions of the present invention are useful in many different applications where hemostatic agents, tissue sealants and tissue adhesives are normally used. The present invention is especially suitable for stopping diffuse capillary bleeding, for example in parenchymal organ bleeding, such as that of the liver, spleen and kidney. In addition, these compositions are useful in treating bleeding associated with debridement during healing of burned tissues.

In one aspect of the present invention, the compositions are useful in controlling diffuse bleeding from cancellous bone surfaces, which are highly vascular and thus prone to excessive post-surgical bleeding. Such bleeding can pose problems during a variety of different surgical procedures, such as in the field of orthopedics, neurosurgery, plastic and reconstructive surgery, spinal surgery and oral-maxillofacial surgery. Post-surgical application of the compositions of the present invention can therefore be used to lessen post-surgical blood loss.

The compositions of the present invention are also useful in controlling intraoperative bleeding that has been exacerbated by genetic or acquired clotting defects or the use of anticoagulation therapy. For example, if a patient receives anticoagulant therapy following surgery and subsequently needs additional surgery, the compositions of the present invention are useful in counteracting the increased bleeding caused by the anticoagulants.

The single-component compositions can be administered directly to the treatment site. Multi-component compositions are preferably premixed, i.e. they are mixed either immediately prior to or during administration, as opposed to being administered in such a manner that all the components come in contact with one another for the first time at the application site. Pre-mixing during administration generally means that the components are either mixed together during delivery while still contained within the delivery device but immediately before exiting the device, or they can be mixed together after exiting the device, but before they contact the application site. In the latter type of device, the contents of two or more compartments can be sprayed from the separate compartments into a single stream of fluid during application. Devices which are suitable for administration of multi-component compositions can be modified to adjust premixing time and efficiency, and are described in U.S. Pat. Nos. 5,116,315; 4,874,368; and 4,359,049.

It is desirable for each of the components of the composition, and especially the collagen-containing component, to be flowable, i.e. to be capable of being administered through a small-gauge orifice, such as a 200–1000 micron opening. To facilitate application by spraying, it is preferable that the compositions be flowable through a 300 micron opening at a flow rate of approximately 1 ml per second. Subsequent gelation allows the compositions to remain in place after application.

The dosage amount will necessarily depend on the particular use for which the composition is being administered, as well as the desired degree of hemostasis, and can be easily determined by a skilled physician.

EXAMPLES

Example 1

Evaluation of Collagen Fiber Size

This experiment was performed to determine the effects of different salt concentrations on the disassembly of collagen fibers. Collagen was purified from bovine corium using pepsin solubilization as described by McPherson, et al., *Collagen Rel. Res.* 5: 119–135 (1985). Following collagen solubilization, fibrillar collagen was reformed by resuspending the soluble (non-fibrillar) collagen in a buffer containing 20 mM sodium phosphate, pH 7.2 The fibers thus formed were harvested by centrifugation and resuspended in water at 20 mg protein/ml.

Several different samples were prepared as indicated below in TABLE III, and the melting temperature of each sample was determined initially after preparation, and after storage for three days at room temperature, using differential scanning calorimetry (DSC). Each sample contained 1–3 mg protein in physiological saline. A total volume of 15 to 30 µl was sealed in pans and heated at 10° C./min in a Mettler TA3000 calorimeter with DSC20 cell (Hightstown, N.J.). A reference sample pan containing the same weight of physiological saline was heated with each sample.

TABLE III

Differential Scanning Calorimetry (DSC)

| Sample No. | Sample Composition | | | Melting Temperature, ° C. | |
|---|---|---|---|---|---|
| | Calcium Chloride, mM | Sodium Chloride, mM | PH | 0 days | 3 days |
| 1 | 0 | 2 | 7.2 | 56.8 | 56.3 |
| 2 | 40 | 2 | 7.2 | 48.3 | 45.0 |
| 3 | 40 | 30 | 7.2 | 50.5 | 49.0 |
| 4 | 100 | 30 | 6.0 | 43.5 | 43.5 |
| 5 | 40 | 150 | 6.3 | 48.4 | 43.8 |

Fibril size was estimated based on the melting temperature results according to Wallace, et al., *Biopolymers*, 25: 1875–1893 (1986.) In general, melting temperatures for microfibrillar collagen are lower than for fibrillar collagen. A melting temperature of 49–50° C. indicates the presence of intermediate-sized fibers, whereas a melting temperature of 44° C. indicates the presence of microfibrillar collagen. According to the DSC results, Sample 2, which contained 40 mM calcium chloride and only 2 mM sodium chloride demonstrated intermediate-sized fibrils at time zero, but had converted to microfibrillar form by day three. In comparison, Sample 3, which contained both calcium chloride and sodium chloride did not exhibit a change in fiber size, which may indicate a counteraction sodium calcium ion mediated fiber disassembly in the presence of sodium chloride. Sample 4, at a calcium chloride concentration of 100 mM, appears to have undergone fiber disassembly prior to the melting temperature being determined. Sample 5, like Sample 2, exhibited a conversion from intermediate-sized fibrils to microfibrils. In Samples 4 and 5, high levels of both salts appeared to promote fibril disassembly, in contrast to Sample 3.

Example 2

Electron Microscopy Studies

Electron microscopy was performed to confirm the state of collagen fibrils in the presence and absence of calcium chloride. In particular, a suspension of fibrillar collagen (20 mg protein/ml) was prepared as described in Example 1. To this suspension, either 25 mM of calcium chloride or an equal volume of water was added. These two test suspensions were incubated at room temperature for 3 weeks to allow disruption of the collagen fibrils.

As observed using electron microscopy, the sample without calcium chloride exhibited loosely woven fibrils, both non-banded and banded, which were 100–250 nm in diameter. In comparison, the sample with calcium chloride exhibited microfibrils which were rarely banded, and which were between 3 and about 30 nm in diameter.

Example 3

Evaluation of Fibrin Clot Strength

This experiment was performed in order to determine the ability of different hemostatic compositions to form fibrin clots. Samples were prepared as described in Example 1 and used after incubation at three days, with the exception of Sample 3 which was used immediately after preparation. All of the samples, except Sample 1, also contained 500 NIH units/ml thrombin. Clot formation was initiated by mixing the hemostatic compositions with an equal volume of rabbit plasma containing sodium citrate at 0.32%, w/v. (Sample 1 was mixed with an equal volume of water to determine the contribution of collagen alone to the gel structure of the clots.) In order to inhibit premature gelation, the pH of the plasma was acidified to 5.0 before mixing with the sample compositions.

After mixing, the sample-plus-plasma mixture was loaded into the sample cell, and the pH was adjusted to 7.2. The sample cell was maintained at 25° C., and measurements were taken after two hours. Rheologic measurements were made in a Rheometrics fluid spectrophotometer, Model 8400 (Piscataway, N.J.). Measurements were taken in dynamic mode in a parallel plane geometry. Gelation was monitored at a 1 radian/sec. oscillation rate and 1% strain, which would not be expected to deform the gel structure. As an indication of the susceptibility of the gel to total breakdown, additional testing was performed at 50% strain.

TABLE IV

Rheometry

| Sample Composition | | Results | | |
|---|---|---|---|---|
| Sample No. | Calcium Chloride, mM | Sodium Chloride, mM | G' at 1% dynes/cm² | G" at 1% dynes/cm² | G' at 50%, dynes/cm² |
| 1 | 0 | 74 | 110 | 46 | 34 |
| 2 | 40 | 52 | 210 | 17 | 480 |
| 3 | 40 | 150 | 310 | 26 | 830 |
| 4 | 40 | 150 | 570 | 66 | 1040 |
| 5 | 114 | 126 | 1010 | 130 | 1300 |

Sample 1, which contained no thrombin or fibrinogen, exhibited a G' value which was indicative of a material with only modest viscous properties. Additionally, as indicated by the decrease of G' at 50% strain, the gel was completely broken down. In contrast, all other samples exhibited a higher G' at 1% strain, with no decrease in G' at 50% strain. These results also indicate a relatively low G", which is indicative of an elastic solid with little viscous character.

Samples 3 and 4 differed only in that Sample 3 was prepared immediately before mixing with plasma, and Sample 4 was stored for three days prior to use. This difference would be expected to demonstrate the effect of fibril size on gel elasticity and strength, Sample 3 having intermediate-sized fibrils and Sample 4 having microfibrils as described in Example 1. As expected, the presence of microfibrils in Sample 4 resulted in formation of a clot with improved elasticity and strength.

In Sample 5, high levels of both salts appear to be able to disassemble fibrils to form micro-fibrils. This is in contrast to an apparent "canceling" effect of calcium and sodium chloride at about 30 mM, as noted before.

Also observed is the direct relationship between the salt concentrations and G' which, when considered in light of the results given in Example 1, indicates that the presence of microfibrillar collagen results in a more elastic clot. Such a clot is expected to be better able to resist displacement by blood flow or other forces that would cause it to be dislodged from the site of application.

Example 4

Effect of PEG on Thrombin Stability

The optional inclusion of PEG enhances the stability of the thrombin in the hemostatic compositions of the present invention. In order to evaluate the differences between PEG of varying size, and at varying concentrations, thrombin activity was evaluated at different time periods after incubation at 18–22° C. Each sample contained Zyderm® Collagen (Collagen Corporation, Palo Alto, Calif.), 40 mM calcium chloride (to convert fibrils to microfibrils) and 500 NIH units/ml thrombin (GenTrac, Inc., Middleton, Wis.), at a pH of 6.4. Thrombin activity was determined using a BBL Fibrosystem fibrometer and an appropriate fibrinogen control, such as Coagulation Control Level 1 (Sigma Chemical Co., Saint Louis, Mo.). A 200 ml aliquot of the fibrinogen control was pre-incubated for 2 min. at 37° C. in the reaction cup, and the reaction was initiated by adding 100 ul of the sample to be tested, after dilution to approximately 5 NIH units/ml with 20 mM HEPES, pH 7.4, 40 mM $CaCl_2$. The fibrometer recorded the time to first fiber formation, which was used to determine thrombin concentration from comparison to a standard curve. Thrombin activity is expressed as a percent of the initial thrombin activity. Thrombin activity after 12 days at room temperature as a function of concentration and molecular weight is presented below in TABLE V.

TABLE V

Effect of PEG on Thrombin Stability

| | Average Molecular Weight of PEG* | | |
|---|---|---|---|
| Concentration | 1000 | 3350 | 8000 |
| 2% | 69 | 48 | 20 |
| 1% | 60 | 42 | 29 |
| 0.5% | 64 | 47 | 22 |
| 0.2% | 90 | 82 | 32 |

*The 1000 and 8000 molecular weight PEG was obtained from Sigma Chemical Company, St. Louis, MO. The 3350 molecular weight PEG was obtained from Union Carbide Chemical Company, South Charleston, WV.

As shown by these results, thrombin activity was greatest at the lowest level of PEG, and using the smaller molecular weight (1000 and 3350) PEG. In a subsequent experiment, aliquots of the sample containing 0.2% PEG-1000 containing 0.02% sodium azide were adjusted to various pHs, between 4.0 and 6.4. The sample at pH 4.0 lost all thrombin activity. The other samples retained over 70% of their activity for up to 45 days.

Later experiments investigated the effect of a lower concentration of PEG-1000 (0.1%), no PEG, PEG-400 (0.2%), PEG-3350 (0.2%) and PEG-8000 (0.2%), all containing 0.02 % sodium azide. Each of these samples retained at least 50% of thrombin activity for up to 30 days.

Example 5

Effect of Microfibrillar Collagen on Platelet Aggregation and Hemostasis

Platelet aggregation was performed with a Model DP-247 E dual Sample Aggregation Meter (Sienco, Inc., Morrison, Company). The scale was adjusted using platelet poor plasma and platelet rich plasma (PRP) as described in the owners manual. A 360 ul aliquot of PRP was heated at 37° C. for 5 min. in a cuvette while stirring. The reaction was then initiated by the addition of 40 ul of the sample. Formulations tested were as follows: Sample 3, described above in Example 1, TABLE III, after 7 weeks incubation and conversion to a micro-fibrillar state (as determined by DSC melting temperature); and a freshly made sample identical to Sample 3, which contained fibrillar collagen, which was diluted with saline to 1 mg/mL. The aggregation of platelets causes an increase in light transmission which is recorded on a strip chart recorder. Efficiency of platelet aggregation is expressed as the time required to reach one-half the maximum transmission (T ½) Using the sample containing fibrillar collagen, T ½ was 2.1 min., in comparison to 1.4 min. for the sample containing microfibrillar collagen.

These same samples were tested in vivo for hemostatic efficiency in an animal model. This study also demonstrated superiority of the sample containing microfibrillar collagen, as indicated by a faster time to achieve hemostasis when compared to the sample containing fibrillar collagen.

Example 6

Platelet Activation

This experiment was performed in order to assess the efficacy of hemostatic compositions of the present invention to form clots in the absence of fibrinogen, but in the presence of platelets. Fresh rabbit blood was centrifuged for 3 minutes at 1380× g, and the platelet rich plasma was separated. This plasma was centrifuged again for 45 minutes at the same speed to pellet the platelets. The plasma-poor supernatant was heated to between 53 and 56° C. for 3 minutes to precipate the fibrinogen. After removing the fibrinogen by centrifugation, the plasma was returned to the platelet pellet. This fibrinogen-depleted plasma, a sample of normal plasma and a 1:1 mixture of the two were all tested for their ability to form fibrin clots.

Plasma samples (or normal saline as a control) were mixed in a 1:1 ratio with a hemostatic composition containing 20 mg/ml collagen, 500 U/mL bovine thrombin and 40 mM $CaCl_2$, and immediately applied to an actively bleeding tissue site in an animal model. The hemostasis times for those sites that stopped bleeding in less than two minutes are shown below in TABLE VI.

TABLE VI

| | | Hemostatic Time | |
|---|---|---|---|
| Platelet Level | Fibrinogen Level | Hemostasis Time, seconds | No. Of Sites No Longer Bleeding After 2 min., #/N |
| Normal | Normal | 48 | 10/10 |
| Normal | 50% of Normal | 49 | 10/10 |
| Normal | Depleted | 51 | 10/10 |
| None | None | 97 | 4/10 |

As demonstrated by these results, even the sample which was combined with plasma depleted of fibrinogen exhibited hemostatic times which were nearly equivalent to those achieved using plasma with normal fibrinogen levels.

Example 7

In Vivo Rabbit Hemostasis

In order to test the ability of the compositions of the present invention to facilitate hemostasis in vivo, the following two-component test composition was prepared: component 1) pepsin-solubilized bovine corium type I collagen was prepared as described in Example 1 above to a final concentration of 20 mg/ml collagen, 40 mM $CaCl_2$ and 500 U/ml bovine thrombin; component 2) rabbit platelet rich plasma, obtained by centrifuging citrated whole blood for 2 minutes at 1380× g. The two components were mixed during application in a two-compartment spraying apparatus. This sample preparation was compared to a conventional two-component fibrin sealant composition comprising lyophilized human fibrinogen (Hemacure, Kirkland, Quebec, Canada) reconstituted to 100 mg/ml protein in deionized water as the first component, and 500 U/ml thrombin in 40 mM $CaCl_2$ as the second component. Also studied were results using Instat™ collagen sponges (Johnson & Johnson Medical, Arlington, Tex.).

The rabbits were anesthetized using standard procedures, and the kidneys and spleen exposed by performing a midline laparotomy. Incisions were made in the kidneys and spleen (2 mm deep by 15 mm long), and pressurized with gauze prior to application of the test samples. The time to hemostasis following administration of the test samples was measured, along with the total blood loss which was determined using preweighed cotton swabs or gauze to absorb the blood from the surgical field. Studies were performed (n=5–6)on untreated rabbits, as well as rabbits that had been pretreated with either asprin or heparin as anticoagulants. The results are reported below in Table VII.

TABLE VII

| Hemostatic Agent | In Vivo Hemostatic Performance* | | | | | |
|---|---|---|---|---|---|---|
| | Normal Coagulation | | Aspirin Treated | | Haparin Treated | |
| | Hemostasis Time (sec) | Blood Loss (ml) | Hemostasis Time (sec) | Blood Loss (ml) | Hemostasis Time (sec) | Blood Loss (ml) |
| Kidney: | | | | | | |
| Test Sample | 27 ± 2 | 0.05 ± 0.16 | 27 ± 4 | 0.1 ± 0.3 | 53 ± 15 | 0.21 ± 0.39 |
| Instat ™ | 78 ± 15 | 0.79 ± 0.76 | 96 ± 12 | 0.8 ± 0.8 | 70 ± 14 | 2.0 ± 1.1 |
| Fibrin Sealant | 68 ± 13 | ND | 147 ± 37 | 1.0 ± 1.6 | 148 ± 37 | 2.0 ± 2.0 |
| None | 225 ± 16 | 2.7 ± 1.9 | 349 ± 42 | 3.6 ± 3.2 | 456 ± 51 | 3.9 ± 2.4 |
| Spleen: | | | | | | |
| Test Sample | 130 ± 25 | 1.1 ± 1.6 | 57 ± 32 | 0 ± 0 | 235 ± 53 | 0.5 ± 0.7 |
| Instat ™ | 122 ± 23 | 0.9 ± 0.6 | 139 ± 41 | 0.5 ± 0.6 | 378 ± 92 | 4.6 ± 2.7 |
| Fibrin Sealant | 152 ± 38 | ND | 145 ± 49 | 0.3 ± 0.4 | 85 ± 66 | 0.3 ± 0.6 |
| None | >600 | 5.4 ± 3.0 | >600 | 4.1 ± 3.0 | >600 | 8.8 ± 3.3 |

*Measurements are reported ± s.e.m.

As shown above in Table VII, the test sample exhibited shorter hemostasis times and less blood loss than either the fibrin sealant or the collagen sponge in the kidney model. In the spleen model, more variability was observed between animals, so comparisons between treatments may not be accurate. However, in all instances, use of the test sample composition showed a significant improvement when compared to untreated animals.

Modifications of the above-described modes for carrying out the invention that are obvious to persons of skill in the field of tissue repair are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A hemostatic composition comprising thrombin and a mixture of non-microfibrillar collagen and microfibrillar collagen in an aqueous medium wherein said microfibrillar collagen has an average fibril diameter of about 3–30 nm.

2. The composition of claim 1, wherein the thrombin is bovine thrombin.

3. The composition of claim 1, wherein the thrombin is recombinant thrombin.

4. The composition of claim 1, wherein the thrombin is a thrombin-like compound.

5. The composition of claim 1, wherein the microfibrillar collagen has an average diameter of about 3–30 nm.

6. The composition of claim 5, wherein the microfibrillar collagen has a melting temperature of about 42 to 46° C.

7. The composition of claim 1 further comprising calcium ions.

8. The composition of claim 7, wherein the calcium ions are present in the form of calcium chloride.

9. The composition of claim 7, wherein the calcium ions are present at a concentration which is effective to disassemble fibrillar collagen into microfibrillar collagen.

10. The composition of claim 1, wherein the thrombin retains 80% or more of its activity after storage at 2–8° C. for at least 6 months.

11. The composition of claim 1 further comprising polyethylene glycol.

12. The compositions of claim 11, wherein the polyethylene glycol has an average molecular weight of about 1,000 to 8,000.

13. The composition of claim 11, wherein the polyethylene glycol is present at a concentration of between 0.1% and 2% w/u.

14. The composition of claim 13, wherein the polyethylene glycol is present at a concentration of between 0.1 and 0.3% w/v.

15. The composition of claim 1, wherein the pH of the composition is between 4.5 and 6.6.

16. The composition of claim 1, wherein the pH of the composition is between 5.0 and 5.7.

17. The composition of claim 1 further comprising at least one sugar, wherein the sugar is present in an amount which is effective to stabilize the thrombin.

18. The composition of claim 1, wherein the sugar is selected from the group consisting of: mannitol, sorbitol, glucose and sucrose.

19. The composition of claim 1 further comprising at least one biologically active agent.

20. The composition of claim 19, wherein the biologically active agent is selected from the group consisting of: growth factors, antibiotics and therapeutic agents.

21. The composition of claim 1, further comprising fibrinogen.

22. The composition of claim 1, further comprising at least one thrombin stabilizer.

23. The composition of claim 22, wherein the thrombin stabilizer is selected from the group consisting of: sugar, a thrombin inhibitor, a calcium chelator and a protein.

24. The composition of claim 1, wherein the composition is flowable through an opening of about 200 to 1000 microns.

25. A kit comprising the composition of claim 1 and a source of fibrinogen.

26. The kit of claim 25, wherein the source of fibrinogen is fibrinogen in an aqueous medium.

27. The kit of claim 25, wherein the source of fibrinogen is plasma.

28. The kit of claim 27, wherein the plasma is human plasma.

29. The kit of claim 27, wherein the plasma is autologous plasma.

30. A kit comprising the composition of claim 1 and a suspension of platelets.

31. The composition of claim 1, wherein the ratio of microfibrillar to non-microfibrillar collagen is at least 1:1 (w/w).

32. The composition of claim 1, wherein the microfibrillar collagen has a fibril diameter of about 3 to 30 nm and a fibril length of about 400 to 500 nm, and wherein the non-microfibrillar collagen has a fibril diameter of at least 30 nm and a fibril length of at least 1000 nm.

33. A method for promoting hemostasis of a tissue site on or in a body of a mammalian subject comprising the steps of:
   (a) providing a hemostatic composition comprising thrombin and microfibrillar collagen in an aqueous medium wherein said microfibrillar collagen has an average fibril diameter of about 3–30 nm;
   (b) providing an aqueous medium comprising fibrinogen;
   (c) mixing the hemostatic composition and the aqueous medium comprising fibrinogen immediately prior to contact with the tissue site; and
   (d) contacting the mixture with the tissue site.

34. The method of claim 33, wherein the aqueous medium comprising fibrinogen is plasma, and the step of providing an aqueous medium comprising fibrinogen further comprises isolating the plasma from the mammalian subject.

35. The method of claim 34, wherein the mammalian subject is a human and the plasma is human plasma.

36. The method of claim 35, wherein the human plasma is isolated from a sample of blood from the human subject.

37. The method of claim 33, wherein the step of mixing takes place in an apparatus during delivery of the hemostatic composition and the aqueous medium comprising fibrinogen to the tissue site.

38. The method of claim 37, wherein the step of mixing takes place after the hemostatic composition and the aqueous medium comprising fibrinogen exit the apparatus, but before the hemostatic composition and the aqueous medium comprising fibrinogen contact the tissue site.

39. A method for promoting hemostasis of a tissue site on or in a body of a mammalian subject comprising the steps of:
   (a) providing a hemostatic composition comprising thrombin and microfibrillar collagen in an aqueous medium wherein said microfibrillar collagen has an average fibril diameter of about 3–30 nm;
   (b) providing an aqueous medium comprising platelets;
   (c) mixing the hemostatic composition and the aqueous medium comprising platelets immediately prior to contact with the tissue site; and
   (d) contacting the mixture with the tissue site.

40. A method of making a composition for use as a hemostatic agent comprising the steps of:
   (a) mixing thrombin, fibrillar collagen and a fiber disassembly agent together in an aqueous medium, wherein the fiber disassembly agent is present at a concentration which is effective at disassembling the fibrillar collagen into microfibrillar collagen; and
   (b) incubating the mixture formed in step (a) for a sufficient length of time and at a sufficient temperature to form microfibrillar collagen having a stable fiber size wherein said microfibrillar collagen has an average fibril diameter of about 3–30 nm.

41. The method of claim 40, wherein the fiber disassembly agent is calcium ions.

42. The method of claim 41, wherein the calcium ions are present at a concentration of between 10 and 200 mM.

43. The method of claim 41, wherein the fiber size of the microfibrillar collagen is between 3 and 30 nm in diameter.

44. The method of claim 40, wherein the method further comprises adding fibrinogen to the aqueous medium.

45. A hemostatic composition comprising thrombin, polyethylene glycol and microfibrillar collagen in an aqueous medium wherein said microfibrillar collagen has an average fibril diameter of about 3–30 nm.

46. The composition of claim 45, wherein the thrombin is bovine thrombin.

47. The composition of claim 45, wherein the thrombin is recombinant thrombin.

48. The composition of claim 45, wherein the thrombin is a thrombin-like compound.

49. The composition of claim 45, wherein the microfibrillar collagen has a melting temperature of about 42 to 46° C.

50. The composition of claim 45 further comprising calcium ions.

51. The composition of claim 50, wherein the calcium ions are present in the form of calcium chloride.

52. The composition of claim 50, wherein the calcium ions are present at a concentration which is effective to disassemble fibrillar collagen into microfibrillar collagen.

53. The composition of claim 45, wherein the thrombin retains 80% or more of its activity after storage at 2–8° C. for at least 6 months.

54. The composition of claim 45, wherein the polyethylene glycol has an average molecular weight of about 1,000 to 8,000.

55. The composition of claim 54, wherein the polyethylene glycol is present at a concentration of between 0.1% and 2% w/v.

56. The composition of claim 55, wherein the polyethylene glycol is present at a concentration of between 0.1 and 0.3% w/v.

57. The composition of claim 45, wherein the pH of the composition is between 4.5 and 6.6.

58. The composition of claim 45, wherein the pH of the composition is between 5.0 and 5.7.

59. The composition of claim 45 further comprising at least one sugar, wherein the sugar is present in an amount which is effective to stabilize the thrombin.

60. The composition of claim 45, wherein the sugar is selected from the group consisting of: mannitol, sorbitol, glucose and sucrose.

61. The composition of claim 45 further comprising at least one biologically active agent.

62. The composition of claim 61, wherein the biologically active agent is selected from the group consisting of: growth factors, antibiotics and therapeutic agents.

63. The composition of claim 45, further comprising fibrinogen.

64. The composition of claim 45, further comprising at least one thrombin stabilizer.

65. The composition of claim 64, wherein the thrombin stabilizer is selected from the group consisting of a sugar, a thrombin inhibitor, a calcium chelator and a protein.

66. The composition of claim 45, wherein the composition is flowable through an opening of about 200 to 1000 microns.

* * * * *